(12) United States Patent
Ching et al.

(10) Patent No.: US 7,306,808 B2
(45) Date of Patent: Dec. 11, 2007

(54) ORIENTIA TSUTSUGAMUSHI TRUNCATED RECOMBINANT OUTER MEMBRANE PROTEIN (R47) AND (R57) VACCINES DIAGNOSTICS AND THERAPEUTICS FOR SCRUB TYPHUS

(75) Inventors: Wei Mei Ching, Bethesda, MD (US); Hong Ge, Gaithersburg, MD (US); Chien-Chung Chao, Bethesda, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/438,345

(22) Filed: May 15, 2003

(65) Prior Publication Data

US 2006/0039920 A1    Feb. 23, 2006

Related U.S. Application Data

(60) Provisional application No. 60/380,301, filed on May 15, 2002.

(51) Int. Cl.
  *A61K 39/02*   (2006.01)
  *A61K 39/00*   (2006.01)
  *A61K 38/00*   (2006.01)
  *C07K 1/00*    (2006.01)

(52) U.S. Cl. .............................. 424/234.1; 424/190.1; 424/184.1; 514/2; 530/350; 530/300; 530/825

(58) Field of Classification Search ................ 530/350, 530/300, 825; 514/2; 424/184.1, 190.1, 424/234.1
See application file for complete search history.

(56) References Cited

U.S. PATENT DOCUMENTS 6,482,415 B1 * 11/2002 Ching et al. ............. 424/234.1

FOREIGN PATENT DOCUMENTS

WO    WO 99/34215    *    7/1999

* cited by examiner

*Primary Examiner*—S. Devi
(74) *Attorney, Agent, or Firm*—Joseph K. Hemby, Jr.; Ning Yang (57) ABSTRACT

A scrub typhus vaccine comprising truncated r47 protein and truncated r56 protein is disclosed. Vaccines composed of r56 protein variants are also disclosed. Methods of reducing HIV viral loads using r47 and r56 proteins and antibodies raised against r47 and r56 are also disclosed.

3 Claims, 6 Drawing Sheets

Figure 2

Induction of r47 protein with IPTG and Fractionation of r47 from crude extract

Figure 3

Fractionation of r47 protein on DEAE anion exchange column (pH 8.0)

Figure 4

Fractionation of r47 protein on DEAE anion exchange column (pH 7.0)

Figure 5

BLAST Search of r47 protein sequence

Figure 6

Comparison of Conserved Domains among r47 and Serine Proteases

ORIENTIA TSUTSUGAMUSHI TRUNCATED RECOMBINANT OUTER MEMBRANE PROTEIN (R47) AND (R57) VACCINES DIAGNOSTICS AND THERAPEUTICS FOR SCRUB TYPHUS

CROSS-REFERENCE TO RELATED APPLICATIONS

This application claims benefit of U.S. Provisional Application No. 60/380,301, filed on 15 May 2002. Other related application includes PCT Application No. PCT/US03/15072, filed on 15 May 2002.

FIELD OF THE INVENTION

The present invention relates to a 47 kDA and a 56 kDA surface protein antigen of *Orientia tsutsugamushi* which are useful as diagnostic antigens as well as immunizing agents. The invention further relates to a therapeutic method of reducing the HIV viral load in a patient.

DESCRIPTION OF THE PRIOR ART

Scrub typhus infection is caused by the obligated intracellular, gram-negative bacterium *O. tsutsugamushi*. It accounts for up to 23% of all febrile episodes in areas of the Asia-Pacific region where scrub typhus is endemic and can cause up to a third of mortality if left untreated. Symptoms may include pneumonitis, meningitis, rash, and headache. Differentiating scrub typhus from other acute febrile illness, such as leptospirosis, murine typhus, malaria, can be difficult because of the similarities in signs and symptoms. Sera from 95-99% of patients with scrub typhus recognize a 56-kDa protein of *O. tsutsugamushi* which comprises 10-15% of the total rickettsial cellular protein content. This 56-kDa protein has both conserved and unique sequences among different strains, has been developed and used for early diagnosis and a potential vaccine candidate.

Whole-organism vaccines have been previously developed and their protections have been short-lived and lack of cross strain protection. The major surface protein antigen, the variable 56-kDa protein which account for the antigenic variation, has been shown to induce protective immunity against the homologous strain but not the heterologous strains. The fact that other antigens, such as 110, 47 and 22 kDa have also been identified with high seroreactivity suggests that a combination of several of these antigens may provide better protection against various stains of *O. tsutsugamushi* infection. Recently, it has been demonstrated that the infusion of plasma from scrub typhus infected patients into HIV infected patients led to the decrease of HIV virus load burden determined 2 months after the initial infusion, suggesting the pharmaceutical effect of the scrub typhus patients' plasma.

SUMMARY OF THE INVENTION

In this report, we have demonstrated the cloning of 47-kDa protein gene, NCBI accession number L31934.1, and the attempt to obtain pure r47, in an effort leading to the production of sufficient quantity and high purity recombinant 47-kDa protein to use in combination with r56 protein as a vaccine candidate to afford broader protection. In addition, the sequence search of this outer membrane protein showed similarity with serine proteases, suggesting r47 protein itself may function as a protease.

Western blot results revealed that plasma from scrub typhus patients showed strong antigenic response to the r47 protein, suggesting a potential protective role of r47 against HIV infection. It is possible that this inhibitory effect was due to the antibody response toward r47 protein. Alternatively, the homology between serine protease and r47 protein indicating a potential protease activity associated with r47 which may result in interference with HIV processing.

A search of the NCBI protein database for short, nearly exact matches revealed a 10-amino-acid match (8 identical and 2 conserved) between the *O. tsutsugamushi* Karp strain 47 kDa antigen (accession number gi/1220501) 47 kDa and HIV envelope protein (accession number gi/2250974) HIVgp120.

Pattern: TLR+IVTN+K

Accordingly, the present inventive subject matter is directed to a scrub typhus immunogenic composition comprising an r47 truncated protein of SEQ ID No. 1, an r56 truncated protein selected from the group consisting of SEQ ID No. 2, SEQ ID No. 3, and SEQ ID No. 4 and a pharmaceutically acceptable carrier.

The present inventive subject matter is further still directed to a method of treating a patient suffering from scrub typhus, the method comprising administering a pharmaceutically effective dose of antibodies raised against the combination of the truncated r47 protein of SEQ ID No. 1 and the truncated r56 protein selected from the group consisting of SEQ ID No. 2, SEQ ID No. 3 and SEQ ID No. 4 and a pharmaceutically acceptable carrier. Alternatively, the method may be comprised of the administration of antibodies raised against either the truncated r47 or the truncated r56 protein.

The present inventive subject matter further contemplates a method for immunizing a subject against scrub typhus comprising administering a pharmaceutically effective amount of a scrub typhus vaccine.

The present inventive subject matter also contemplates an assay for detecting antibodies to scrub typhus comprising obtaining a sample from a subject, exposing the sample to r47 protein as a complement to an r56 assay in assay equipment selected from the group consisting of ELISA plates, dot-blot matrices, and hand held chromatographic and flow through assay devices.

The present inventive subject matter further contemplates a treatment of an HIV patient which comprises a truncated r47 protein of SEQ ID No. 1 and a pharmaceutically acceptable carrier which results in a reduction of the HIV viral load of an HIV patient.

The present inventive subject also contemplates a treatment of an HIV patient which comprises an r56 protein selected from the group of SEQ ID No. 2, SEQ ID No. 3, SEQ and SEQ ID No. 4.

The present inventive subject matter further contemplates an HIV vaccine comprising a potential HIV vaccine and a truncated r47 or r56 protein or protein combinations thereof.

The foregoing and other features and advantages will become further apparent from the following detailed description of the presently preferred embodiments, when read in conjunction with the accompanying examples and made with reference to the accompanying drawings. It should be understood that the detailed description and examples are illustrative rather than limitative, the scope of the present invention being defined by the appended claims and equivalents thereof.

DETAILED DESCRIPTION OF THE PREFERRED EMBODIMENTS

Scrub typhus of *tsutsugamushi* disease is an acute, febrile disease caused by infection with *Orientia tsutsugamushi*. *O. tsutsugamushi* is a gram-negative bacterium but has neither lipopolysaccharide nor a peptidoglycan layer. *Orientia* isolates are highly variable in their antigenic properties. The major surface protein of *O. tsutsugamushi* is the variable 56-kDA protein. Serotype-specific monoclonal antibodies to *Orientia* react with the 56-kDA protein. Although sera from most patients with scrub typhus recognize this protein, another 47-kDA protein is also recognized, suggesting that both 56-kDA and 47-kDA proteins are good candidates for use as diagnostic antigens and that the combination of these two proteins has potential use as an immunogenic composition.

In accordance with the present invention, there is generally provided a scrub typhus immunogenic composition comprising an r47 truncated protein of SEQ ID No. 1, an r56 truncated protein; and a pharmaceutically acceptable carrier.

The 47 kDa antigen is a membrane protein. In order to produce a properly folded r47 protein in aqueous solution, its n-terminus which contains the hydrophobic domain was truncated. Forward primer SEQ ID NO. 5 and reverse primer, SEQ ID NO. 6, were designed to amplify the gene segment of nucleotides 174-1481, SEQ ID NO. 7. The amplified gene segment was cloned into pET24a vector. The expressed protein sequence is in SEQ ID NO. 1.

In embodiments of the inventive subject matter, the scrub typhus immunogenic composition may comprise the r47 truncated protein in combination with one of the following r56 truncated proteins: SEQ ID No. 2, SEQ ID No. 3, or SEQ ID No. 4 and a pharmaceutically acceptable carrier.

Dosing and Administration

The optimum dose of the immunogenic composition is contemplated to be 0.5-20 mg for humans and 0.5-2.5 mg for primates. Administration of the immunogenic composition is done subcutaneously.

The inventive subject matter also provides an assay for detecting antibody to scrub typhus comprising obtaining a sample from a subject, exposing the sample to a truncated r47 protein as represented in SEQ ID No. 1 in assay equipment. Such assay equipment may be selected from the group consisting of ELISA plates, dot-blot matrices, and hand held chromatographic and flow through assay devices. Samples suitable for such assay methods include blood, oral fluids and urine from which antibodies could be detected and from which antigens could be detected by way of laboratory generated antibodies.

The inventive subject matter further comprise a method of treating a patient suffering from scrub typhus, the method comprising administering a pharmaceutically effective dose of antibodies raised against the combination of truncated proteins of SEQ ID No. 1 and the truncated r56 protein selected from the group consisting of SEQ ID No. 2, SEQ ID No. 3 and SEQ ID No. 4 and a pharmaceutically acceptable carrier.

The inventive subject matter also contemplates a pharmaceutical composition for treatment of an HIV patient comprising antibodies raised against a truncated r56 protein and a pharmaceutically acceptable carrier wherein administration of the composition reduces the patients viral load. Such truncated proteins may be selected from the group consisting of SEQ ID Nos. 2-4 or combinations thereof. The dosing and administration are the same as stated above for the immunogenic compositions.

The present inventive subject matter further contemplates a treatment of an HIV patient which comprises antibodies raised against a truncated r47 protein selected from the group of SEQ ID No. 1 and a pharmaceutically acceptable carrier which results in a reduction of the HIV viral load of an HIV patient. Dosing and administration are also as stated above for this embodiment.

The inventive subject matter also contemplates treatment of an HIV patient which comprises administering a pharmaceutical composition comprising antibodies raised against a combination of an r47 truncated protein and a truncated r56 protein and a pharmaceutically acceptable carrier to reduce the patients HIV viral load. Dosing and administration are also as stated above for this embodiment.

The inventive subject matter also contemplates an immunogenic composition against HIV infection comprising a pharmaceutical effective dose of antibodies raised against a truncated r47 protein and a truncated r56 protein of SEQ ID Nos. 2-4 and combinations thereof. Dosing and administration are as stated above for this embodiment.

The following examples are illustrative of preferred embodiments of the invention are not to be construed as limiting the invention thereto.

EXAMPLES

Example 1

Forward and reverse DNA primers (SEQ ID No. 5-6, respectively) specific for 47-kDa (accession no. L31934.1) were designed with BamH1 and NcoI (both from NEB) restriction sites and used for PCR to amplify the gene coding for a truncated 47-kDa protein using DNA purified from Karp strain of *O. tsutsugamushi*. The PCR product (insert) was ligated to plasmid pET24d (Novagen™) digested with BamH1 and NcoI. The sequence of insert was confirmed and the ligated plasmid was transformed into BL21 (DE3) cells (Invitrogen™). Colony containing ligated plasmid was grown 2YT medium and induced with 1 mM of IPTG at 37° C. for 3 h for protein expression. To purify this expressed protein, 600 ml of B121(DE3) cells were grown, induced, centrifuged and cell pellet was lysed with 20 mM Tris-HCL (pH 8.0) containing 5 mM EDTA and 1 mM PMSF according to the method developed by Ching et al., Clin. Diag. Lab. Immuno. 5, 519-526, 1998. After ultrasonic disruption and centrifugation, the expressed protein was mainly associated with supernatant rather than inclusion body. This fraction was further purified with a 30,000 MW cutoff membrane follow by DEAE anion exchange using 2 mM Tris pH 8.0 and 2M NaCl salt gradient (Agilent 1100 HPLC). Alternatively, the protein was separated on a DEAE anion exchange using 20 mM Tris pH 7.0 and 2M NaCl salt gradient. The protein eluted with salt gradient was collected, analyzed with SDS-PAGE, and stained with coomassie blue to identify the purity of each fraction. In some cases, different fractions were poured together for the SDS-PAGE analysis.

The sequence homology of 47-kDa protein with other known proteins was searched with standard BLAST method and the conserved domain analysis of 47-kDa protein was analyzed using NCBI CDD algorithm. (FIGS. 5-6) In addition, proteins with similar domains as 47-kDa protein were aligned together to analyze the conserved amino acid sequence within the family.

Results

Figure 1A:
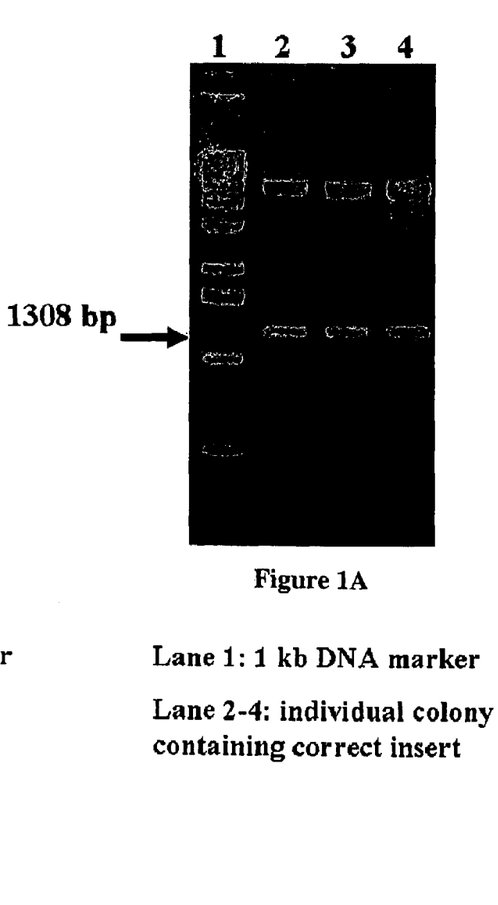
FIG. 1A is an SDS-PAGE showing the PCR product of DNA coding for the truncated 47-kDa protein.
Figure 1B:
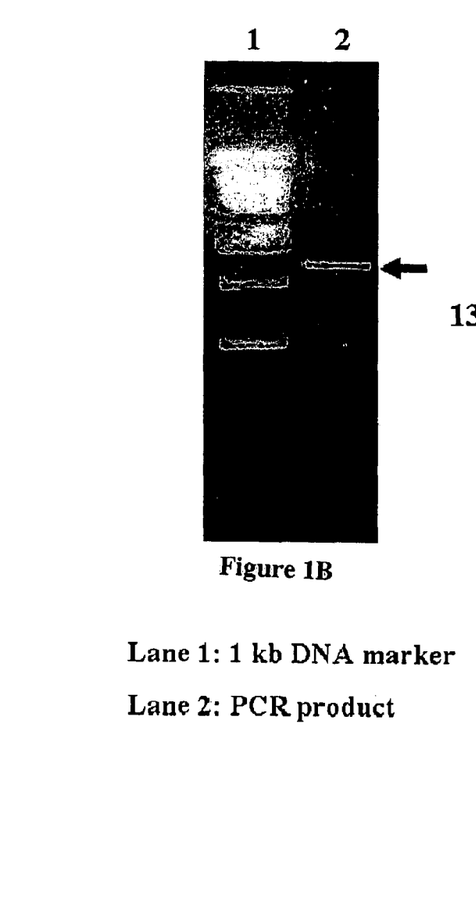
FIG. 1B is an SDS-PAGE showing the PCR product of DNA coding for the digested plasmids.

The DNA coding for 47-kDa protein was successfully PCR amplified using DNA purified from O. tsutsugamushi Karp strain as template and primers designed specifically for this genes (FIG. 1). The cloning of this PCR product into Pet24d(+) plasmid was confirmed after digestion with BamH1 and NcoI (FIG. 1) and DNA sequence was verified with a DNA sequencer.

Figure 2:
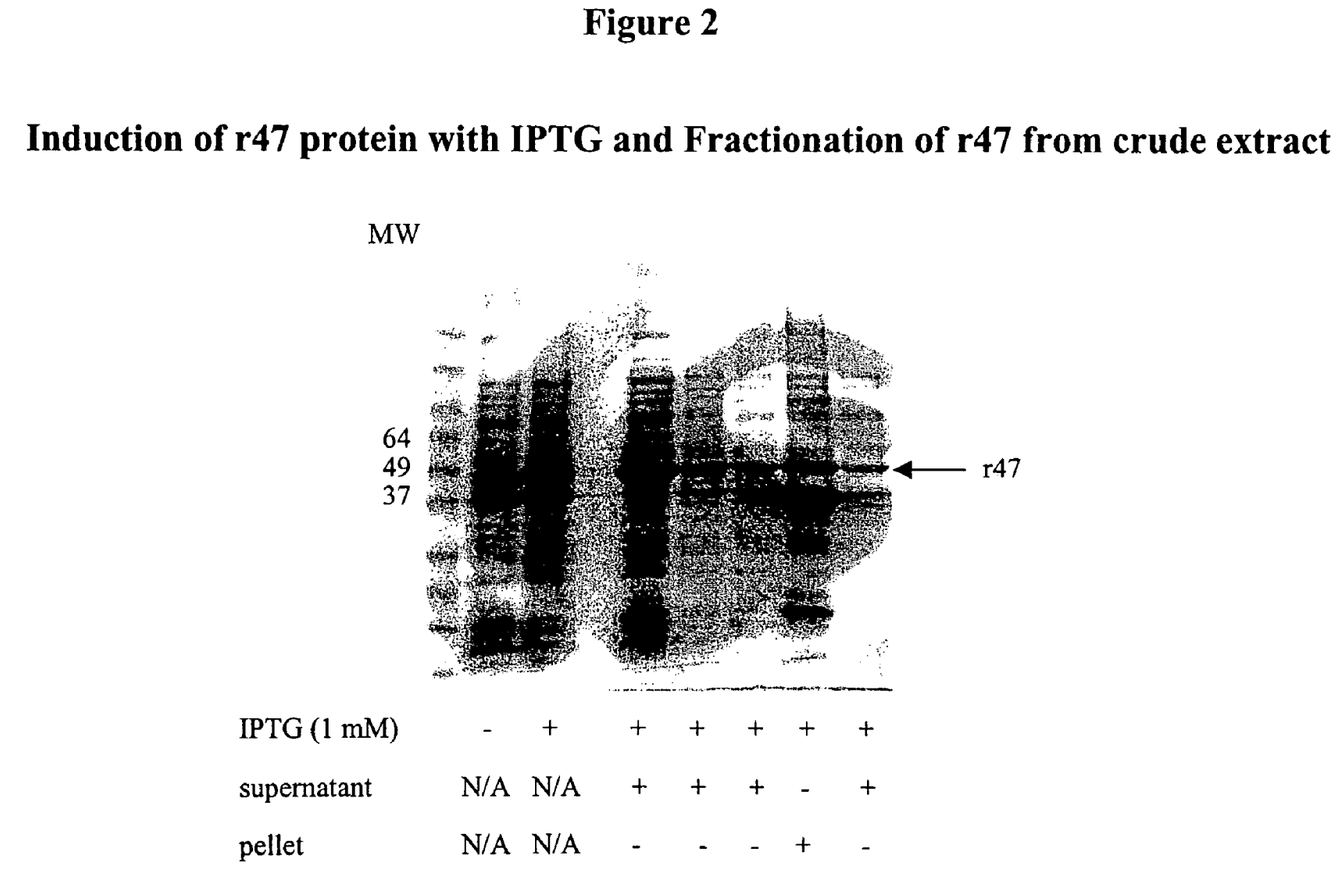
FIG. 2 is An SDS-PAGE showing the induction of r47 protein with IPTG and fractionation of r47 from crude extract.
Figure 3:
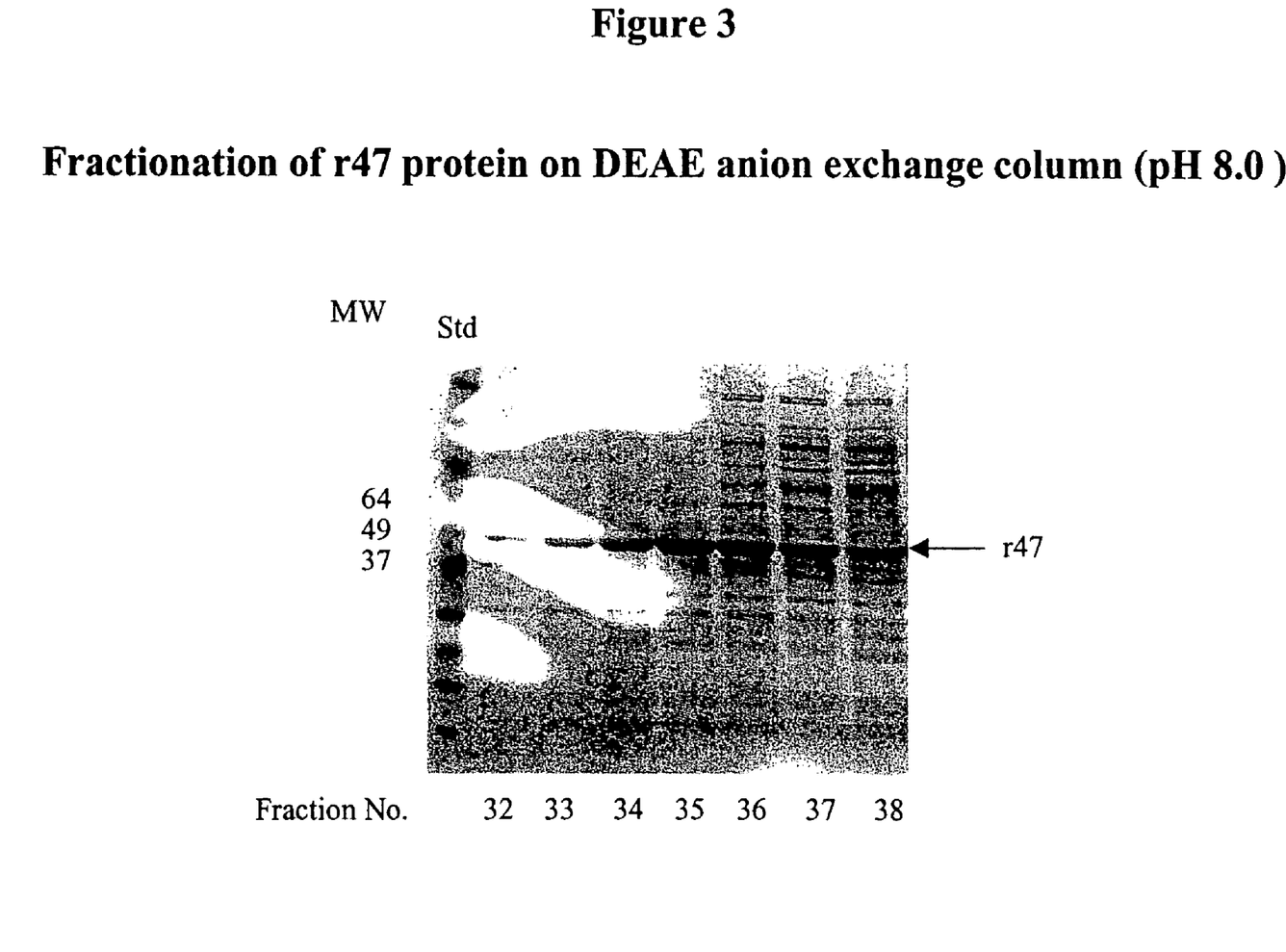
FIG. 3 is an SDS-PAGE showing fractionation of r47 protein on DEAE anion exchange column (pH 8.0)
Figure 4:
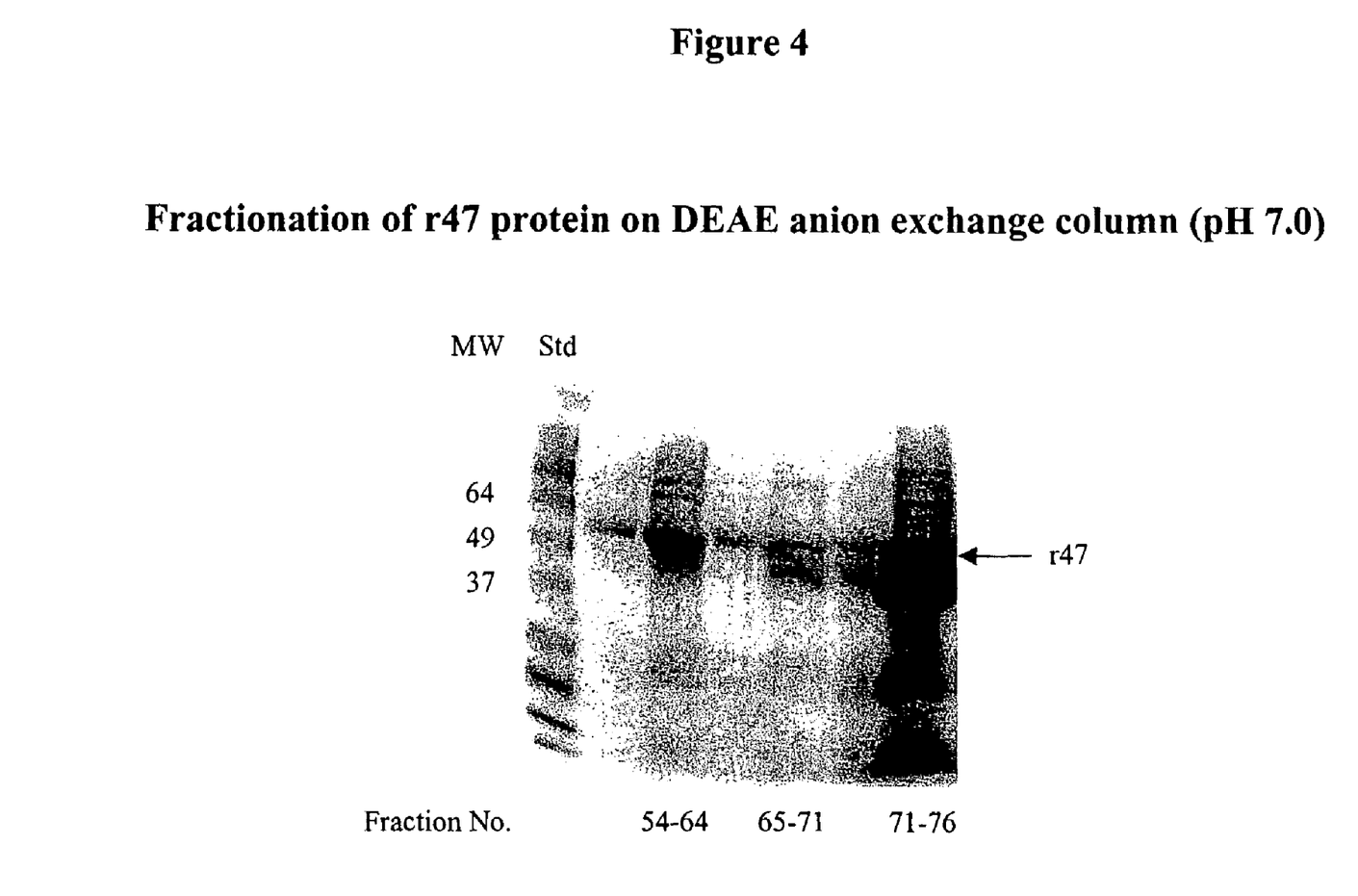
FIG. 4 is an SDS-PAGE showing fractionation of r47 protein DEAE anion exchange column (pH 7.0)

Expression of the 47-kDa protein was observed after 3 h of 1 mM IPTG induction at 37° C. (FIG. 2). The sequence of this expressed protein was confirmed with protein sequencer. (After sonication and centrifugation, the expressed protein was mainly associated with supernatant after the first centrifugation (FIG. 2) rather than associated with inclusion body as the r56 protein reported by Ching et al. The expressed protein may be associated with the membrane fraction and the addition of detergent (1% of NP40) appears to increase the yield during purification procedure (data not shown). Part of the supernatant containing r47 was first purified with DEAE anion exchange on a HPLC using a Tris buffer at pH 8.0 and protein was eluted with a NaCl gradient (up to 0.8 mM) and the fractions were collected and analyzed with SDS-PAGE (FIG. 3). The other part of the supernatant was purified with HPLC using a Tris buffer at pH 7.0 and eluted with a NaCl gradient (up to 2 M). The resulted fractions were poured and analyzed for r47 (FIG. 4).

Figure 5:
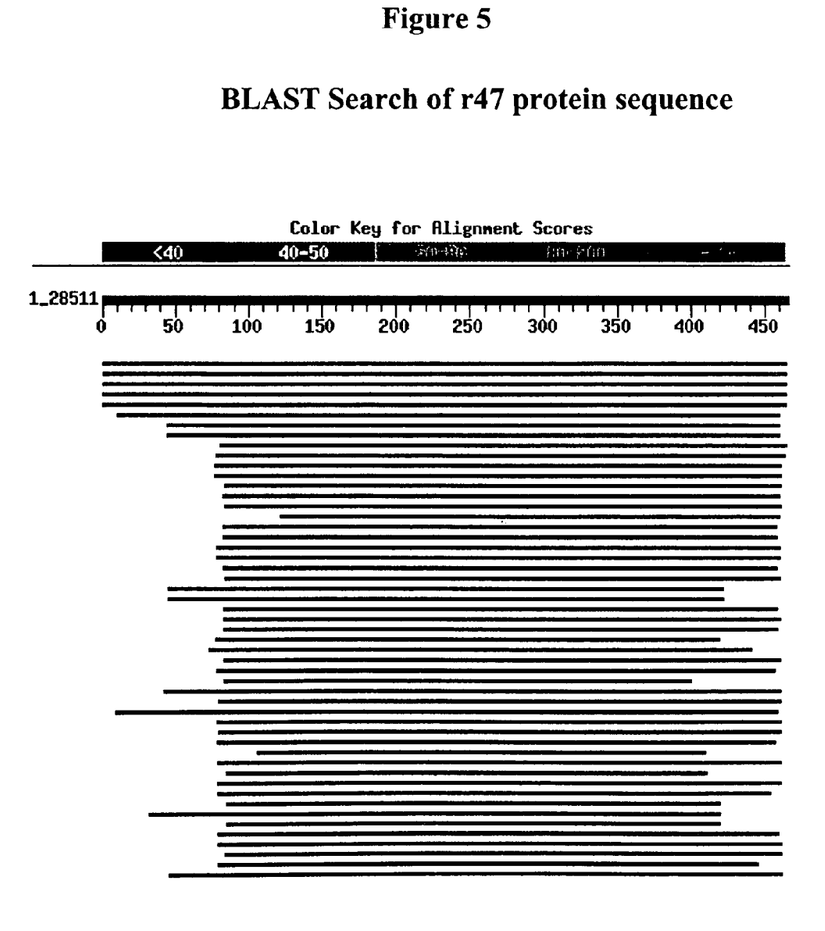
FIG. 5 is a Blast Search of r47 protein sequence.
Figure 6:
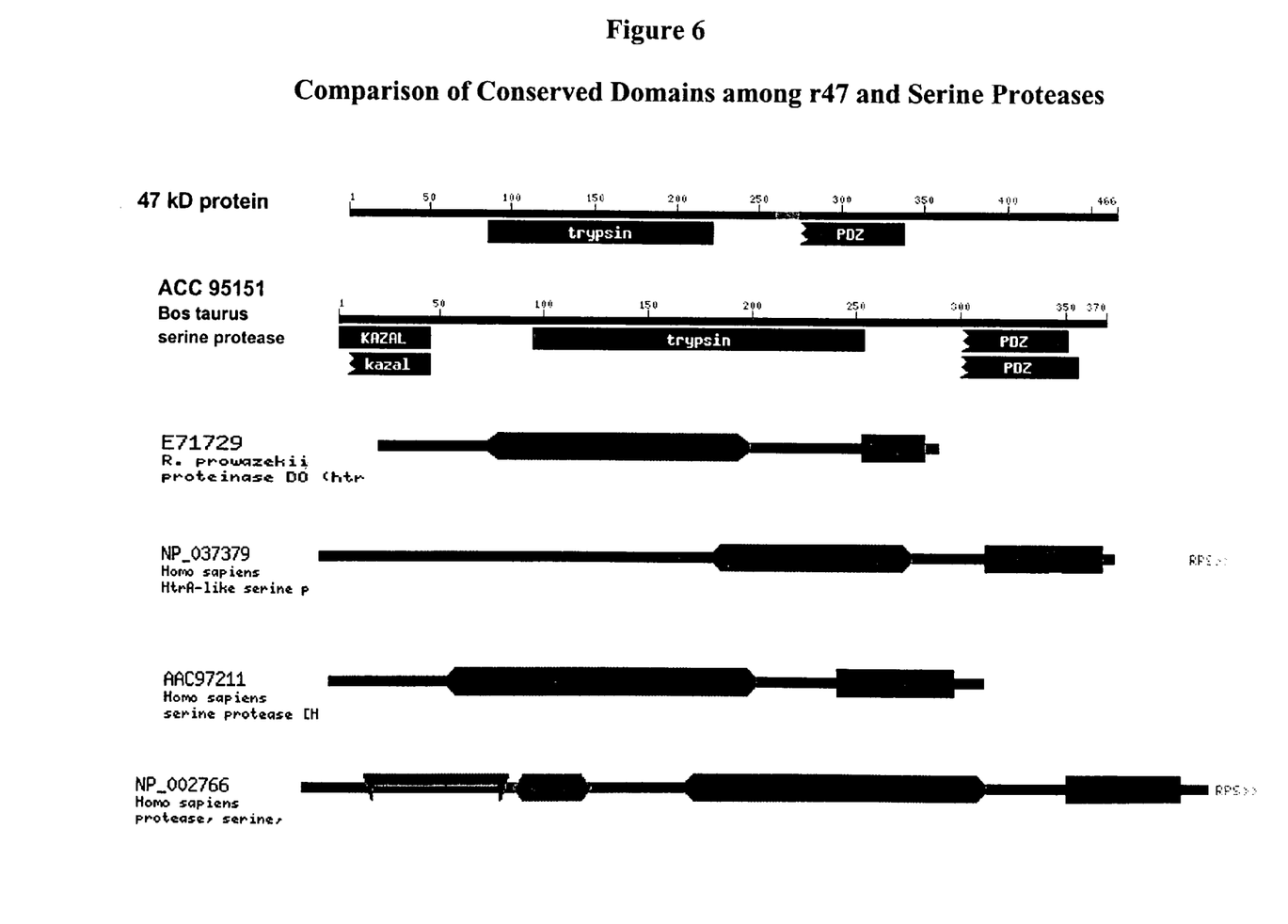
FIG. 6 is a chart comparing conserved domains among r47 and serine proteases.

The search of similarity of r47 with standard BLAST resulted in homologues with various serine proteases (FIG. 5). When r47 was searched against protein conserved domain database maintained by NCBI, a trypsin-line (77.7% of the conserved domain region (217 residues) was aligned) and PDZ domain (73.3% of the conserved domain region (86 residues) was aligned) were identified. These two domains were also associate with different serine proteases (FIG. 6).

Example 2

Assessment of Homologous Protection Induced by Recombinant 56 kDa Protein from Orientia tsutsugamushi in Combination with 47 kDa Scrub Typhus Antigens In order to assess the protective effect of r56 and r47 proteins against infection, mice will receive varying doses of r56 and r47 protein components from the Karp strain. Since the immunization with 25 ug or 2 ug of r56 in mice showed a protective role in our previous experiments (Annual Report J2_00_NMRC), we will use the same doses for testing r56 in the present study. For the r47 proteins, we do not know the optimum doses, but we will start with two dosages of 5 ug and 25 ug at this time. Alum and CpG will be used as adjuvants at the ratio of protein: Al +3: CpG=1: 25: 10. Alum has been approved for human use for a long time. Vaccines prepared by antigens adsorbed onto ALHYDROGEL have several advantages. The antigenic content is easier to standardize and the vaccine has good stability. ALHYDROGEL adsorbed antigens are simple and more convenient to use. In addition, the degree of local reaction following immunization is reduced. CpG induces a Th1-like pattern of cytokine production dominated by IL-12 and IFN-gamma with little secretion of Th2 cytokines. Female CD1 mice, 4 to 5 weeks old, 13 to 15 grams in weight, will be purchased from Charles River Laboratories (Wilmington, Mass.). Each Study included 5-7 groups of mice. A minimum of 15-20 mice is needed to down select the 20% difference in protective efficacy at 80-85% confidence level. Each group of 20 mice will be immunized i.m. with the 56 kDa antigen alone or in combination with r47 antigen except for the negative control groups. 15 mice will be challenged 4 weeks later and 5 mice will be sacrificed for measuring T-cell immune responses right before challenge.

Detailed experimental designs:

Study 1 (5 groups):
1. Negative control: PBS only
2. 25 ug of r56 only
3. 25 ug of 47 kDa only Study 2 (7 groups):
1. Negative controls: the same as the group 1 in Study 1
2. 25 ug of r56, plus 5 ug of 47 kDa
3. 25 ug of r56, plus 25 ug of 47 kDa Study 3 (5 groups):
1. Negative control: PBS only
2. 2 ug of r56 only
3. 4.2 ug of 47 kDa only Study 4 (7 groups):
1. Negative controls: the same as the group 1 in Study 1
2. 2 ug of r56, plus 5 ug of 47 kDa
3. 2 ug of r56, plus 2 ug of 47 kDa 3) Monitoring the Immune Response:

(a) Antibody Detection: Mouse sera will be drawn immediately before immunization and before challenge. Each serum sample will be assayed in duplicate by enzyme-linked immunosorbent assay (ELISA) for antibodies against each antigen. Anti-mouse IgG and IgM peroxidase-labeled conjugate (Boehringer-Mannheim, Indianapolis, Ind.) will be tested.

(b) Cytokine detection in serum: Cytokines have been studied physiologically and pathologically with a focus on the roles in immune regulation during inflammation. IFN gamma and IL-4 are cytokines for Th1 and Th2 cells, respectively. For many intracellular infections, IL-12 may induce Th1 response, i.e. IFN-gamma production. The levels of IFN gamma and IL-2 were elevated in spleen mononuclear cells from 56 kDa immunized mice. Increased IFN was also detected in spleen cells and lymph nodes cells from mice chronically infected with Orientia. It was noted that Orientia was susceptible to INF gamma in cultured mouse cells. In the sera of patients with scrub typhus infection, the levels of G-CSF, M-CSF, IFN gamma, and TNF alpha were up regulated. Mice blood will be drawn in heparin before immunization, 2, 4, 6, 8, 10, 15, and 30 days after immunization. Sera samples will be assayed in duplicate for cytokine levels of IFN gamma, TNF alpha, IL-4, IL-12, G-CSF, and M-CSF.

(c) Cytokine production by antigen specific T-cells: Spleen mononuclear cells (SMNC), stimulated by recombinant antigens, will be monitored for the productions of IFN gamma and IL-2 at day 1, 2, and 3 post stimulation. The cells will be isolated by FICOLL-HYPAQUE (PHARMACIA™, Uppsala, Sweden) density gradient centrifugation. After washing, the cells will be resuspended to a concentration of 5×10E6 per ml in warm RPMI-10, and 100 ul will be distributed in each well of a 96-well plate as described. Following incubation with corresponding recombinant antigens, culture supernatants will be collected and used in cytokine assays. The supernatants from triplicate SMNC cultures will be pooled, and all samples will be assayed in triplicate. IL-2 activity in the supernatants from antigen-stimulated SMNC will be tested for its ability to support growth of IL-2-dependent CTLL-2 cells in the presence of anti-IL-4 antibody (11B11; 10 ug/ml). For INF-gamma and IL-4, the levels will be measured by enzyme-linked immunosorbent assay kit (GENZYME, Boston, Mass.) according to the manufacturer's instructions. CD4 and CD8 cells will be selected to determine which cells are producing the cytokines using MACS direct MicroBeads (MILTENYI BIOTEC®, Auburn Calif.).

(d) Proliferative response of spleen cells: SMNC will be prepared as described above. After the stimulation by different amounts of recombinant protein or *Orientia* Karp, the cultures will be incubated at 37 C for 72 h under a humidified atmosphere of 5% CO2. A total of 1 uCi of [3H] thymidine will be added to each well for the another 18 h of culture. Cells will be harvested onto glass fiber filter strips, and incorporation of [3H] thymidine will be counted in a liquid scintillation counter.

Prophetic Example 3

Prophetic examples for the treatment of HIV patient to reduce the virus load with immunoglobulins from subjects immunized by the immunogenic composition.

There is no animal model for HIV infection at the present time. However, transgenic mice carrying the human CD-4 gene can be infected by HIV. This type of mice will be used in the following experiments:

Mice will be infected with HIV. Two months later, one group of mice will be treated with hyper immune plasma from the same type of mice immunized by the said immunogenic composition (group 1). Another group of mice will be treated with normal plasma to serve as the control group (group 2). Blood will be drawn from both groups at one week interval for four times. The HIV load in the blood will be quantitated by real time PCR. Results from group 1 will be compared to group 2 to demonstrate the dereased virus load by the hyper immune plasma.

CONCLUSIONS

The truncated 47-kDa protein was successfully cloned and overexpressed in BL21 cells. The over expressed protein was not in the inclusion body making the purification procedure complicated. The addition of detergent increased the amount of r47 suggesting the association of protein with membrane fraction. Although dialysis of crude extract with 25,000 MW cutoff offered some purification and further purification using pH 8.0 or pH 7.0 buffer and salt gradient on an anion exchange column resulted in further purification, the protein was not yet fully purified. The pI of r47 was predicted to be 8.2 and suggested a cation exchange is more suitable for purification. Experiments will continue to purify r47 with cation exchange followed by gel filtration to achieve desired purity.

The computer disc contains sequence numbers 1-9. The sequence listing information recorded in computer readable form is identical to the written sequence listing in the specification and includes no new matter.

The inventive subject matter being thus described, it will be obvious that the same may be varied in many ways. Such variations are not to be regarded as a departure from the spirit and scope of the inventive subject matter, and all such modifications are intended to be within the scope of the following claims.

What is claimed is:

1. An immunogenic composition comprising:
   an isolated truncated r47 protein of *Orientia tsutsugamushi* having the amino acid sequence set forth in SEQ ID NO: 1;
   an isolated truncated r56 protein of *Orientia tsutsugamushi* having the amino acid sequence set forth in SEQ ID NO: 2, SEQ ID NO: 3, or SEQ ID NO: 4; and
   a pharmaceutically acceptable carrier.

2. An immunogenic composition comprising:
   an isolated recombinant truncated r47 protein of *Orientia tsutsugamushi* having the amino acid sequence set forth in SEQ ID NO: 1;
   isolated truncated r56 proteins of *Orientia tsutsugamushi* selected from SEQ ID NO: 2, SEQ ID NO: 3, and SEQ ID NO: 4; and
   a pharmaceutically acceptable carrier.

3. A method of immunizing a subject against scrub typhus comprising administering a pharmaceutically effective amount of the immunogenic composition of claim 1 or claim 2.

* * * * *

SEQUENCE LISTING

<160> NUMBER OF SEQ ID NOS: 7

<210> SEQ ID NO 1
<211> LENGTH: 425
<212> TYPE: PRT
<213> ORGANISM: orientia tsutsugamushi
<220> FEATURE:
<221> NAME/KEY: MISC_FEATURE
<223> OTHER INFORMATION: Expressed, truncated protein sequence
      (translated from 184-1458 of DNA seqence, boded sequence was
      confirmed by N-terminal protein sequenceing)

<400> SEQUENCE: 1

Met Val Asn Ser Leu Ser Asp Ile Val Glu Pro Leu Ile Ser Thr Val
1               5                   10                  15

Val Ser Ile Tyr Ala Val Asp Thr Asn Ile Gly Ile Ser Phe Asn Asn
            20                  25                  30

Lys Val Ser Lys Tyr Gln Gln Glu Val Phe Leu Gly Ser Gly Val Ile
        35                  40                  45

Ile Asp Ser Ser Gly Tyr Ile Val Thr Asn Glu Asn Val Ile Ala Gly
    50                  55                  60

Ala Glu Asn Ile Lys Val Lys Leu His Asp Gly Ser Glu Leu Ile Ala
65                  70                  75                  80

```
Glu Leu Val Gly Ser Asp Asn Lys Ile Asn Ile Ala Leu Leu Lys Ile
                 85                  90                  95

Asn Ser Pro Ala Ala Leu Ser Tyr Ala Thr Phe Gly Asp Ser Asn Gln
            100                 105                 110

Ser Arg Val Gly Asp Gln Val Ile Ala Ile Gly Ser Pro Phe Gly Leu
        115                 120                 125

Arg Gly Thr Val Thr Asn Gly Ile Ile Ser Ser Lys Gly Pro Asp Met
130                 135                 140

Gly Asn Gly Ile Val Thr Asp Phe Ile Gln Thr Asn Ala Ala Ile His
145                 150                 155                 160

Met Gly Ser Phe Gly Gly Pro Met Phe Asn Leu Glu Lys Ile Ile
                165                 170                 175

Gly Ile Asn Ser Ile His Val Ser Tyr Ser Gly Ile Ser Phe Ala Ile
            180                 185                 190

Pro Ser Asn Thr Val Leu Glu Ala Val Glu Cys Leu Lys Lys Gly Glu
        195                 200                 205

Lys Ile Arg Arg Gly Met Leu Asn Val Met Leu Asn Glu Leu Thr Pro
210                 215                 220

Glu Leu Asn Glu Asn Leu Gly Leu Lys Gln Asp Gln Asn Gly Val Leu
225                 230                 235                 240

Ile Thr Glu Val Ile Lys Glu Gly Ser Ala Ala Gln Cys Gly Ile Ala
                245                 250                 255

Pro Gly Asp Val Ile Thr Lys Phe His Asp Lys Glu Ile Lys Thr Gly
            260                 265                 270

Arg Asp Leu Gln Val Ala Val Ser Ser Thr Met Leu Asn Ser Glu Arg
        275                 280                 285

Glu Val Glu Leu Leu Arg Asn Gly Lys Ser Met Thr Leu Lys Cys Lys
290                 295                 300

Ile Ile Ala Asn Lys Gly Glu Asp Ser Glu Gln Gln Ser Asn Asp Gln
305                 310                 315                 320

Ser Leu Val Val Asn Gly Val Lys Phe Val Asp Leu Thr Pro Asp Leu
                325                 330                 335

Val Lys Lys Tyr Asn Ile Thr Ser Ala Asn Asn Asn Gly Leu Phe Val
            340                 345                 350

Leu Glu Val Ser Pro Asn Ser Ser Trp Gly Arg Tyr Gly Leu Lys Met
        355                 360                 365

Gly Leu Arg Pro Arg Asp Ile Ile Leu Ser Val Lys Arg Asp Asp Asn
370                 375                 380

Lys Lys Asp Ile Ser Val Lys Thr Leu Arg Glu Ile Val Thr Asn Ile
385                 390                 395                 400

Lys His Asn Glu Ile Phe Phe Thr Val Gln Arg Gly Asp Arg Met Leu
                405                 410                 415

Tyr Ile Ala Leu Pro Asn Ile Asn Lys
            420                 425

<210> SEQ ID NO 2
<211> LENGTH: 376
<212> TYPE: PRT
<213> ORGANISM: Unknown
<220> FEATURE:
<223> OTHER INFORMATION: r56 Protein Karp (Ching)

<400> SEQUENCE: 2

Met Thr Ile Ala Pro Gly Phe Arg Ala Glu Ile Gly Val Met Tyr Leu
1               5                   10                  15
```

```
Thr Asn Ile Thr Ala Gln Val Glu Glu Gly Lys Val Lys Ala Asp Ser
             20                  25                  30

Val Gly Glu Thr Lys Ala Asp Ser Val Gly Gly Lys Asp Ala Pro Ile
         35                  40                  45

Arg Lys Arg Phe Lys Leu Thr Pro Pro Gln Pro Thr Met Pro Ile Ser
 50                  55                  60

Ile Ala Val Arg Asp Phe Gly Ile Asp Ile Pro Asn Ile Pro Gln Gln
 65                  70                  75                  80

Gln Ala Gln Ala Ala Gln Pro Gln Leu Asn Asp Glu Gln Arg Ala Ala
                 85                  90                  95

Ala Arg Ile Ala Trp Leu Lys Asn Cys Ala Gly Ile Asp Tyr Arg Val
                100                 105                 110

Lys Asn Pro Asn Asp Pro Asn Gly Pro Met Val Ile Asn Pro Ile Leu
            115                 120                 125

Leu Asn Ile Pro Gln Gly Asn Pro Asn Pro Val Gly Asn Pro Pro Gln
130                 135                 140

Arg Ala Asn Pro Pro Ala Gly Phe Ala Ile His Asn His Glu Gln Trp
145                 150                 155                 160

Arg His Leu Val Val Gly Leu Ala Ala Leu Ser Asn Ala Asn Lys Pro
                165                 170                 175

Ser Ala Ser Pro Val Lys Val Leu Ser Asp Lys Ile Thr Gln Ile Tyr
            180                 185                 190

Ser Asp Ile Lys His Leu Ala Asp Ile Ala Gly Ile Asp Val Pro Asp
            195                 200                 205

Thr Ser Leu Pro Asn Ser Ala Ser Val Glu Gln Ile Gln Asn Lys Met
210                 215                 220

Gln Glu Leu Asn Asp Leu Leu Glu Glu Leu Arg Glu Ser Phe Asp Gly
225                 230                 235                 240

Tyr Leu Gly Gly Asn Ala Phe Ala Asn Gln Ile Gln Leu Asn Phe Val
                245                 250                 255

Met Pro Gln Gln Ala Gln Gln Gly Gln Gly Gln Gln Gln Gln Gln Ala
            260                 265                 270

Gln Ala Thr Ala Gln Glu Ala Val Ala Ala Ala Val Arg Leu Leu
            275                 280                 285

Asn Gly Asn Asp Gln Ile Ala Gln Leu Tyr Lys Asp Leu Val Lys Leu
290                 295                 300

Gln Arg His Ala Gly Ile Lys Lys Ala Met Glu Lys Leu Ala Ala Gln
305                 310                 315                 320

Gln Glu Glu Asp Ala Lys Asn Gln Gly Glu Gly Asp Cys Lys Gln Gln
                325                 330                 335

Gln Gly Thr Ser Glu Lys Ser Lys Gly Lys Asp Lys Glu Ala Glu
            340                 345                 350

Phe Asp Leu Ser Met Ile Val Gly Gln Val Lys Leu Tyr Ala Asp Val
            355                 360                 365

Met Ile Thr Glu Ser Val Ser Ile
370                 375
```

<210> SEQ ID NO 3
<211> LENGTH: 529
<212> TYPE: PRT
<213> ORGANISM: Unknown
<220> FEATURE:
<223> OTHER INFORMATION: r56 Protein Sequence (Kato)

<400> SEQUENCE: 3

-continued

```
Met Lys Lys Ile Met Leu Ile Ala Ser Ala Met Ser Ala Leu Ser Leu
1               5                   10                  15

Pro Phe Ser Ala Ser Ala Ile Glu Leu Gly Asp Glu Gly Gly Leu Glu
            20                  25                  30

Cys Gly Pro Tyr Ala Lys Val Gly Val Gly Gly Met Ile Thr Gly
        35                  40                  45

Val Glu Ser Thr Arg Leu Asp Pro Ala Asp Ala Gly Gly Lys Lys Gln
    50                  55                  60

Leu Pro Leu Thr Thr Ser Met Pro Phe Gly Gly Thr Leu Ala Ala Gly
65                      70                  75                  80

Met Thr Ile Ala Pro Gly Phe Arg Ala Glu Leu Gly Val Met Tyr Leu
                85                  90                  95

Ala Asn Val Lys Ala Glu Val Glu Ser Gly Lys Thr Gly Ser Asp Ala
            100                 105                 110

Asp Ile Arg Ser Gly Ala Asp Ser Pro Met Pro Gln Arg Tyr Lys Leu
            115                 120                 125

Thr Pro Pro Gln Pro Thr Ile Met Pro Ile Ser Ile Ala Asp Arg Asp
    130                 135                 140

Leu Gly Val Asp Ile Pro Asn Val Pro Gln Gly Gly Ala Asn His Leu
145                 150                 155                 160

Gly Asp Asn Leu Gly Ala Asn Asp Ile Arg Arg Ala Asp Asp Arg Ile
            165                 170                 175

Thr Trp Leu Lys Asn Tyr Ala Gly Val Asp Tyr Met Val Pro Asp Pro
            180                 185                 190

Asn Asn Pro Gln Ala Arg Ile Val Asn Pro Val Leu Leu Asn Ile Pro
            195                 200                 205

Gln Gly Pro Pro Asn Ala Asn Pro Arg Gln Ala Met Gln Pro Cys Ser
    210                 215                 220

Ile Leu Asn His Asp His Trp Arg His Leu Val Val Gly Ile Thr Ala
225                 230                 235                 240

Met Ser Asn Ala Asn Lys Pro Ser Val Ser Pro Ile Lys Val Leu Ser
            245                 250                 255

Glu Lys Ile Val Gln Ile Tyr Arg Asp Val Lys Pro Phe Ala Arg Val
            260                 265                 270

Ala Gly Ile Glu Val Pro Ser Asp Pro Leu Pro Asn Ser Ala Ser Val
        275                 280                 285

Glu Gln Ile Gln Asn Lys Met Gln Glu Leu Asn Asp Ile Leu Asp Glu
    290                 295                 300

Ile Arg Asp Ser Phe Asp Gly Cys Ile Gly Gly Asn Ala Phe Ala Asn
305                 310                 315                 320

Gln Ile Gln Leu Asn Phe Arg Ile Pro Gln Ala Gln Gln Gly Gln
            325                 330                 335

Gly Gln Gln Gln Gln Gln Ala Gln Ala Thr Ala Gln Glu Ala Ala Ala
        340                 345                 350

Ala Ala Ala Val Arg Val Leu Asn Asn Asn Asp Gln Ile Ile Lys Leu
            355                 360                 365

Tyr Lys Asp Leu Val Lys Leu Lys Arg His Ala Gly Ile Lys Lys Ala
    370                 375                 380

Met Glu Glu Leu Ala Ala Gln Asp Gly Gly Cys Asn Gly Gly Asp
385                 390                 395                 400

Asn Lys Lys Lys Arg Gly Ala Ser Glu Asp Ser Asp Ala Gly Gly Ala
            405                 410                 415

Ser Lys Gly Gly Lys Gly Lys Glu Thr Lys Glu Thr Glu Phe Asp Leu
```

```
                   420                 425                 430
Ser Met Ile Val Gly Gln Val Lys Leu Tyr Ala Asp Leu Phe Thr Thr
            435                 440                 445

Glu Ser Phe Ser Ile Tyr Ala Gly Leu Gly Ala Gly Leu Ala Tyr Thr
        450                 455                 460

Ser Gly Lys Ile Asp Gly Val Asp Ile Lys Ala Asn Thr Gly Met Val
465                 470                 475                 480

Ala Ser Gly Ala Leu Gly Val Ala Ile Asn Ala Ala Glu Gly Val Tyr
                485                 490                 495

Val Asp Ile Glu Gly Ser Tyr Met His Ser Phe Ser Lys Ile Glu Glu
            500                 505                 510

Lys Tyr Ser Ile Asn Pro Leu Met Ala Ser Phe Gly Val Arg Tyr Asn
        515                 520                 525

Phe

<210> SEQ ID NO 4
<211> LENGTH: 524
<212> TYPE: PRT
<213> ORGANISM: Unknown
<220> FEATURE:
<223> OTHER INFORMATION: r56 Protein (Gilliam)

<400> SEQUENCE: 4

Met Lys Lys Ile Met Leu Ile Ala Ser Ala Met Ser Ala Leu Ser Leu
1               5                   10                  15

Pro Phe Ser Ala Ser Ala Ile Glu Leu Gly Glu Gly Gly Leu Glu
            20                  25                  30

Cys Gly Pro Tyr Gly Lys Val Gly Ile Val Gly Gly Met Ile Thr Gly
        35                  40                  45

Ala Glu Ser Thr Arg Leu Asp Ser Thr Asp Ser Glu Gly Lys Lys His
    50                  55                  60

Leu Ser Leu Thr Thr Gly Leu Pro Phe Gly Gly Thr Leu Ala Ala Gly
65                  70                  75                  80

Met Thr Ile Ala Pro Gly Phe Arg Ala Glu Leu Gly Val Met Tyr Leu
                85                  90                  95

Arg Asn Ile Ser Ala Glu Val Glu Val Gly Lys Gly Lys Val Asp Ser
            100                 105                 110

Lys Gly Glu Ile Lys Ala Asp Ser Gly Gly Gly Thr Asp Thr Pro Ile
        115                 120                 125

Arg Lys Arg Phe Lys Leu Thr Pro Pro Gln Pro Thr Ile Met Pro Ile
    130                 135                 140

Ser Ile Ala Asp Arg Asp Val Gly Val Asp Thr Asp Ile Leu Ala Gln
145                 150                 155                 160

Ala Ala Ala Gly Gln Pro Gln Leu Thr Val Glu Gln Arg Ala Ala Asp
                165                 170                 175

Arg Ile Ala Trp Leu Lys Asn Tyr Ala Gly Ile Asp Tyr Met Val Pro
            180                 185                 190

Asp Pro Gln Asn Pro Asn Ala Arg Val Ile Asn Pro Val Leu Leu Asn
        195                 200                 205

Ile Thr Gln Gly Pro Pro Asn Val Gln Pro Arg Pro Arg Gln Asn Leu
    210                 215                 220

Asp Ile Leu Asp His Gly Gln Trp Arg His Leu Val Val Gly Val Thr
225                 230                 235                 240

Ala Leu Ser His Ala Asn Lys Pro Ser Val Thr Pro Val Lys Val Leu
                245                 250                 255
```

Ser Asp Lys Ile Thr Lys Ile Tyr Ser Asp Ile Lys Pro Phe Ala Asp
        260                 265                 270

Ile Ala Gly Ile Asp Val Pro Asp Thr Gly Leu Pro Asn Ser Ala Ser
        275                 280                 285

Val Glu Gln Ile Gln Ser Lys Met Gln Glu Leu Asn Asp Val Leu Glu
        290                 295                 300

Asp Leu Arg Asp Ser Phe Asp Gly Tyr Met Gly Asn Ala Phe Ala Asn
305                 310                 315                 320

Gln Ile Gln Leu Asn Phe Val Met Pro Gln Gln Ala Gln Gln Gln Gln
                325                 330                 335

Gly Gln Gly Gln Gln Gln Ala Gln Ala Thr Ala Gln Glu Ala Val
        340                 345                 350

Ala Ala Ala Ala Val Arg Leu Leu Asn Gly Asn Asp Gln Ile Ala Gln
        355                 360                 365

Leu Tyr Lys Asp Leu Val Lys Leu Gln Arg His Ala Gly Val Lys Lys
        370                 375                 380

Ala Met Glu Lys Leu Ala Ala Gln Gln Glu Glu Asp Ala Lys Asn Gln
385                 390                 395                 400

Gly Glu Gly Asp Cys Lys Gln Gln Gly Ala Ser Glu Lys Ser Lys
                405                 410                 415

Glu Gly Lys Gly Lys Glu Thr Glu Phe Asp Leu Ser Met Ile Val Gly
        420                 425                 430

Gln Val Lys Leu Tyr Ala Asp Leu Phe Thr Thr Glu Ser Phe Ser Ile
        435                 440                 445

Tyr Ala Gly Val Gly Ala Gly Leu Ala His Thr Tyr Gly Lys Ile Asp
        450                 455                 460

Asp Lys Asp Ile Lys Gly His Thr Gly Met Val Ala Ser Gly Ala Leu
465                 470                 475                 480

Gly Val Ala Ile Asn Ala Ala Glu Gly Val Tyr Val Asp Leu Glu Gly
                485                 490                 495

Ser Tyr Met His Ser Phe Ser Lys Ile Glu Glu Lys Tyr Ser Ile Asn
                500                 505                 510

Pro Leu Met Ala Ser Val Gly Val Arg Tyr Asn Phe
        515                 520

```
<210> SEQ ID NO 5
<211> LENGTH: 31
<212> TYPE: DNA
<213> ORGANISM: Unknown
<220> FEATURE:
<223> OTHER INFORMATION: Forward Primers
<220> FEATURE:
<221> NAME/KEY: misc_feature
<223> OTHER INFORMATION: Gene (125-174 as target gene sequence)
      Nco I site

<400> SEQUENCE: 5
tatgcatacc atggtaaata gtttatctga t                              31

<210> SEQ ID NO 6
<211> LENGTH: 35
<212> TYPE: DNA
<213> ORGANISM: UNKNOWN
<220> FEATURE:
<223> OTHER INFORMATION: Reverse primers
<220> FEATURE:
<221> NAME/KEY: misc_feature
<223> OTHER INFORMATION: Gene sequence of 1443-1477 as target, 35 bp
      BamH1 site
```

-continued

```
<400> SEQUENCE: 6
cgcctggatc ctagatttac ttattaatat taggt                               35

<210> SEQ ID NO 7
<211> LENGTH: 1307
<212> TYPE: DNA
<213> ORGANISM: UNKNOWN
<220> FEATURE:
<223> OTHER INFORMATION: PCR
<220> FEATURE:
<221> NAME/KEY: misc_feature
<223> OTHER INFORMATION: PCR amplified sequence: 174-1481 nt. Expressed
      DNA sequence: 184-1458 nt, aa 42-466. the coding region is bold

<400> SEQUENCE: 7
tatgcatatt atggtaaata gtttatctga tatagttgag ccattaatat ctacagtagt     60
aagtatttat gctgtagata ctaacattgg tattagtttt aataataagg tatctaagta    120
tcagcaagaa gtgttcttag gttctggggt tatcattgat agttctgggt atattgttac    180
taatgagaat gttatagcag gagctgaaaa tataaaagta aagttgcatg atggttcaga    240
actcatagca gaattagttg gtagtgacaa taaaattaat atagctttat taaaaattaa    300
ttctccagca gcattatctt atgcgacttt tggcgactca aatcagtcta gagtaggaga    360
tcaggttatt gcaataggaa gtccttttgg tttaagagga acagtaacaa atggcattat    420
ttcttctaaa ggaccagata tgggtaacgg catagtaact gattttattc aaactaatgc    480
tgctattcat atgggtagct ttggtggacc gatgtttaat cttgaaggaa aaattattgg    540
aattaattcc attcacgtat cttactcagg cataagtttt gctattccat ctaatactgt    600
acttgaagca gttgaatgct taaaaaaagg agaaaaaatt cgtcgtggta tgttaaatgt    660
tatgcttaat gaattaactc cagaattaaa tgagaattta ggacttaaac aagatcaaaa    720
tggagttcta ataactgaag ttataaaaga aggatctgca gcacaatgtg gaattgctcc    780
tggagatgta attactaaat ttcatgataa agagatcaaa acagggagag atttacaggt    840
agctgtatct tcaactatgc ttaattctga aagagaagtt gagcttttac gtaatggtaa    900
gtcgatgact ctaaaatgta aaattattgc caacaaaggt gaggatagtg agcaacaaag    960
taatgatcaa agccttgtgg ttaatggtgt aaaatttgtt gatcttacac ctgatttagt   1020
gaagaaatat aatattactt cagctaataa taatgggtta tttgtccttg aagtttcgcc   1080
taactcttct tgggggagat atggtttaaa aatgggcta agacctagag atataaatttt   1140 atcagttaaa cgtgatgata taaaaaaaga tatttctgtt aaaactctaa gagaaatagt   1200
gacaaatata aagcataatg aaattttctt tacagtgcaa agaggagata gaatgctttta   1260 cattgcttta cctaatatta ataagtaaat ctagtttaaa ggcgatt                 1307
```